United States Patent [19]

Walters

[11] Patent Number: 4,522,715
[45] Date of Patent: Jun. 11, 1985

[54] HIGH PERFORMANCE CHROMATOGRAPHY COLUMN

[75] Inventor: Rodney R. Walters, Ames, Iowa

[73] Assignee: Iowa State University Research Foundation, Inc., Ames, Iowa

[21] Appl. No.: 640,925

[22] Filed: Aug. 14, 1984

Related U.S. Application Data

[63] Continuation of Ser. No. 495,646, May 18, 1983, abandoned.

[51] Int. Cl.³ .............................................. B01B 15/08
[52] U.S. Cl. ..................................... 210/198.2; 55/386
[58] Field of Search ................. 210/656, 198.2; 55/67, 55/197, 386; 285/86, 109, 55, 126

[56] References Cited

U.S. PATENT DOCUMENTS

| | | | |
|---|---|---|---|
| 2,328,468 | 8/1943 | Laffly | 285/126 |
| 2,349,081 | 5/1944 | Douglass | 285/86 |
| 3,381,980 | 5/1969 | Smith | 285/109 |
| 3,472,533 | 10/1969 | Turner | 285/55 |
| 3,855,130 | 12/1974 | Randau et al. | 210/198.2 |
| 3,904,527 | 9/1975 | Wilhelmson | 210/198.2 |
| 4,280,905 | 7/1981 | Gunkel | 210/198.2 |
| 4,313,828 | 2/1982 | Brownlee | 210/198.2 |
| 4,389,313 | 6/1983 | Charney | 210/198.2 |
| 4,399,032 | 8/1983 | Mott | 210/198.2 |

Primary Examiner—John Adee
Attorney, Agent, or Firm—Zarley, McKee, Thomte, Voorhees & Sease

[57] ABSTRACT

A chromatography column adapted to be used in high performance liquid chromatography which includes an elongated tubular hollow column of rigid material which is enclosed by an outer tubular sleeve. End fittings are removably attachable to opposite ends of the outer tubular sleeve and have longitudinal passageways extending through their length, said passageways terminating in an enlarged bore at their innermost ends wherein ring means are insertable. Opposite ends of the column are also insertable into the enlarged bores of the end fittings. The end fittings are adjustably securable to opposite ends of the sleeve so that opposite ends of the column are brought into secure and sealing abutment with the ring means which in turn are sandwiched against the end fittings. A passageway for the circulation of fluids is thus formed through the end fitting ring means and column and tubular means can be sealingly secured to the longitudinal passageways at the outer ends of the end fittings to integrate the chromatography column with a high performance liquid chromatography system.

13 Claims, 4 Drawing Figures

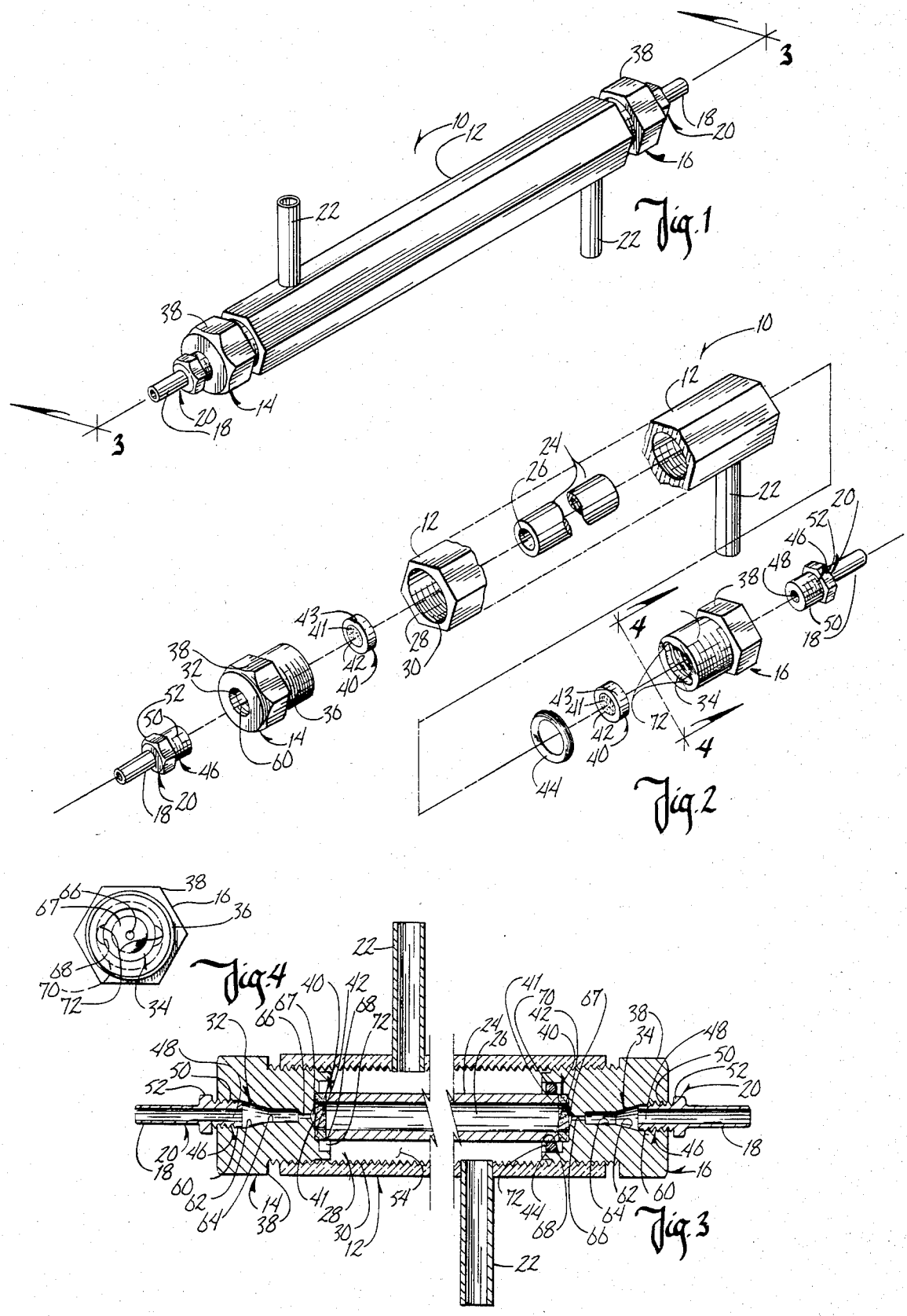

HIGH PERFORMANCE CHROMATOGRAPHY COLUMN

This is a continuation, of application Ser. No. 495,646, filed May 18, 1983, abandoned.

BACKGROUND OF THE INVENTION

This invention relates to high performance liquid chromatography, and more particularly, to chromatography columns adapted to be used in high performance liquid chromatography.

Columns or column blanks are utilized as part of high pressure liquid chromatography systems. The columns assist in the analyzation of mixtures and are of different diameters and lengths for different uses.

Traditional high performance liquid chromatography (HPLC) columns are rigid elongated tubes having threaded opposite interior ends to which threaded end fittings can be attached. These threaded end fittings have longitudinal passageways extending through their lengths and are adapted to receive fluid carrying tubes which transport the liquid mixture to be analyzed to and from the column. Alternatively female threaded couplers are secured around the column blank at opposite ends to receive the end fittings. Ferrules are mounted on the column ends to seal the column to the end fittings. These traditional commercial HPLC columns are not suitable because the end fittings and/or threads and/or ferrules occupy a space of several centimeters on the column blank and thus limit how short the column can be. Commercial columns are available generally in the range of 5-30 centimeters in length. Needs have arisen for columns of only a few millimeters in length and therefore these traditional columns are not able to satisfy this need.

Additionally, traditional HPLC columns are subject to damage because of the constant coupling and uncoupling of the end fittings and therefore are subject to leakage around the ferrules. Because certain instances require columns of varying inside diameter, not only are a variety of different columns needed but also the end fittings have to be changed to matingly seal with the column ends.

U.S. Pat. No. 4,280,905 utilizes a column which is encased by an outer sleeve which has threaded outside surfaces at opposite ends. End caps having threaded interior bores are then threaded down upon the opposite ends of the sleeve and compress seals against the ends of the column. This device also has a sealing means which seals the sleeve from the outside in order that pressure can be applied between the inner column and the outer sleeve. Although this design eliminates the problems associated with having a threaded column, it does not eliminate the problem of limiting how short the column can be because the outer screw caps tighten over the sleeve and therefore restrict how short the sleeve can be which therefore limits how short the column can be while maintaining a sealing relationship.

It is therefore an object of this invention to provide a column for high performance liquid chromatography which improves upon the deficiencies in the prior art.

Another object of this invention is to provide a column for high performance liquid chromatography which may be as short as a few millimeters in length.

Another object of this invention is to provide a column for high performance liquid chromatography which is not limited in how short it can be by the sleeve or end fittings.

A further object of this invention is to provide a column for high performance liquid chromatography which eliminates ferrules in the column.

A further object of this invention is to provide a column for high performance liquid chromatography which allows columns of varying inside diameters to be used with the same end fittings and sleeve.

Another object of this invention is to provide a column for high performance liquid chromatography which allows some variation in length of column utilizing the same fittings and sleeve.

Another object of this invention is to provide a column for high performance liquid chromatography which allows column blanks without threads or any other permanently affixed fittings to be used.

Another object of this invention is to provide a column for high performance liquid chromatography which allows the use of columns of substantially varying lengths while only requiring the use of different sleeves but utilizing the same end fittings.

A further object of this invention is to provide a column for high performance liquid chromatography which is not susceptible to damage or deformation of the inside of the column.

Another object of this invention is to provide a column for high performance liquid chromatography which improves upon the prior art substantially reducing the risk of leaks.

A further object of this invention is to provide a column for high performance liquid chromatography which can withstand high pressures without leaking.

Another object of this invention is to provide a column for high performance liquid chromatography wherein the parts most subject to damage or wear are cheaply and easily replaceable.

A further object of this invention is to provide a column for high performance liquid chromatography which is economical, efficient and durable.

Additional objects, features and advantages of the invention will become apparent with reference to the accompanying specification and drawings.

SUMMARY OF THE INVENTION

This invention utilizes an elongated rigid tubular hollow column which is encased inside of a hollow elongated sleeve. End fittings are removably securable to opposite ends of the sleeve and have longitudinal passageways extending therethrough. These end fittings also hold sealing rings in compressive abutment to opposite ends of the column. A passageway is therefore formed through the end fittings, rings and column and allows tubular members to be attached to the outer ends of either end fittings to communicate fluids to and from the column.

The end fittings thus are adjustable so as to hold the column sealingly against the sealing rings without having any direct attachment to the column. By utilizing the added option of using different size sleeves, the adjustability of the end caps allows the length of the column to be as short as a few millimeters long and still be held in sealing compressive abutment.

BRIEF DESCRIPTION OF THE DRAWINGS

FIG. 1 is a perspective view of the invention in its assembled state.

FIG. 2 is an unassembled perspective view with a cutaway of the sleeve showing the column.

FIG. 3 is a sectional view taken along lines 3—3 of FIG. 1.

FIG. 4 is an end view taken along lines 4—4 of FIG. 2.

DETAILED DESCRIPTION OF THE PREFERRED EMBODIMENT

In reference to the drawings, and particularly FIG. 1, there is shown a column for high performance liquid chromatography 10 in accordance with the invention. In an assembled state as shown in FIG. 1, a sleeve member 12 being of elongated shape and having a hollow interior has two end fittings 14 and 16 secured at opposite open ends. Tubes 18 having fittings 20 in turn are secured into end fittings 14 and 16 and carry the fluids to be analyzed to and away from the invention 10. Tube connectors 22 can be optionally attached to the system 10 to provide entrance and exits for fluid such as water into the sleeve member 12.

Referring now to FIG. 2, the parts of the invention 10 can be more clearly seen. Column blank or column 24 is an elongated rigid tube having a bore 26 extending therethrough. Column 24 is encased by sleeve member 12 having bore 28. In the preferred embodiment, the interior surface of sleeve member 12 is threaded with threads 30.

End fittings 14 and 16 are generally cylindrical and have passageways 32 and 34 extending longitudinally therethrough, respectively. The exteriors of end fittings 14 and 16 are threaded with threads 36 except for their outer ends which comprise nut elements 38 which are configured to allow conventional wrenches to grip and turn end fittings 14 and 16. Ring means 40 are circular in shape having hollow bores 42 extending therethrough in which are secured frit members 41 and are insertable into the passageways 32 and 34 at the interior ends of end fittings 14 and 16. O-ring 44 is also insertable into passageway 34 of end fitting 16.

Fittings 20 include a cylindrical member 46 having a passageway 48 extending longitudinally through. Threads 50 are imposed on the exterior surface of cylindrical members 46 except for nut elements 52 which again are configured to allow conventional wrenches to grip and secure and turn.

In the preferred embodiment, column 24 is a one quarter inch outside diameter type 316 stainless steel column blank with ends cut on a lathe. It is to be understood, however, that in high performance liquid chromatography various column lengths and inside diameters are desired for different applications. In traditional liquid chromatography systems, column 24 would be anywhere from 5–30 cm in length. The invention 10 allows the column to be as short as is technically possible, which is desired for some applications, with columns as short as approximately 5 mm having been used. Additionally, inside diameter of the column 24 can be varied for different uses, sometimes ranging from as small as 2.1 mm to 4.6 mm inside diameter.

In the preferred embodiment, sleeve member 12 is a $\frac{3}{4}$ inch hexagonal brass connector with $\frac{3}{8}$ inch-32 threads on its inside surface. Its length is typically $\frac{1}{2}$ inch greater than the length of column 24. The inside diameter of sleeve member 12 is larger than the outside diameter of column 24 to allow for a space 54 between the outer walls of column 24 and the inner walls of sleeve member 12. (See FIG. 3). By utilizing tube connectors 22 (FIGS. 1 and 3) a water jacket can be created around column 24. Sleeve member 12 can also be of different lengths depending upon the length of column 24.

End fittings 14 and 16 are $\frac{3}{4}$ inch hexagonal type 304 stainless steel with threads 30 being $\frac{3}{8}$ inch-32 threads. End fittings 14 and 16 are thus threadably insertable into threaded bore 28 at opposite ends of sleeve member 12.

Ring means 40 are $\frac{1}{4}$ inch outside diameter fluorocarbon-encased stainless steel frits and can be obtained from Alltech Associates, Inc., in Deerfield, Ill. Ring means 40 are sandwiched between end fitting 14 and 16 and opposite ends of column 24 when end fittings 14 and 16 are threadably tightened down into sleeve member 12. Ring means 40 can be comprised of middle circular frit members 41 being of fused or partially fused materials such as steel which does allow fluids to pass and outer rings 43 of a fluorocarbon material.

Fittings 20 are 1/16 inch Swagelok male fittings and are threadably securable into threaded passageways 32 and 34 of end fittings 14 and 16.

FIG. 3 shows the structural cooperation of the invention 10. Passageways 32 and 34 of end fittings 14 and 16 consist of five different diametered bores. Outer bores 60 are threaded and of a diameter to matingly accept threaded fittings 20. Bores 62 are conical in shape and narrow the diameters of passageways 32, 34 as they decrease to bores 64. Small bores 66 are 0.0135 inch diameter bores and open into a tapered opening of diameter of 0.08 inches and a depth of 0.015 inches (designated by reference numeral 67). Finally, inner ring bores 68 are enlarged bores adjacent to openings 67 and extend to the inner end of end fittings 14, 16 and are of a diameter to matingly hold ring means 40 and column 24 when inserted therein. Additionally, end fitting 16 has an annular slot 70 surrounding enlarged bore section 68. Annular slot 70 securely holds O-ring 44 in place. O-ring 44 is made of a resilient material such as rubber and in the preferred embodiment is $\frac{1}{4}$ inch inside diameter by 1/16 inch. This size of O-ring 44 will allow column 24 to be inserted therethrough, slightly resiliently expanding to allow such insertion but remaining of a sufficient inside diameter to secure itself around column 24 and hold column 24 in a relatively secure manner in end fitting 16 even if end fitting 14 is moved.

In operation, the invention 10 functions as follows. In one primary use, the invention 10 is used for slurry column packing. A slurry mixture of slush-like consistency is packed into column 24 to aid in analyzation of the liquid mixture. To pack column 24, end fitting 14 with ring means 40 is removed from sleeve member 12 and a slurry packing end fitting (not shown) having a slightly larger fourth section bore 66 (for example 0.030 in.) is then inserted with a ring means 40 back into sleeve member 12. Ring member 40 in this use is a fluorocarbon ring made from a frit from which the central steel portion has been removed. The remainder of invention 10 is assembled as shown in FIG. 3. After packing of column 24 is accomplished by injecting the slurry through tube 18 and fitting 20 which are attached to the slurry packing end fitting, the slurry packing end fitting is removed. It is at this point that the O-ring 44, if used, helps prevent the packed column 24 from being pulled out of end fitting 16. The invention 10 is then reassembled using regular end fitting 14 and ring means 40 (frit).

Invention 10 is then attached to tubes 18 and fittings 20 and is ready for injection of the mixture to be analyzed.

It should be noted that end fittings 14 and 16 can contain tweezer channels 72 which are machined on opposite sides of passageways 32 and 34 on the inner ends of end fittings 14 and 16 so that tweezers can be used in channels 72 when a frit or O-ring needs to be removed. Tweezer channels 72 are more clearly shown in FIG. 4. Also, when a water jacket or other substance is desired to be inserted surrounding column blank 24 in space 54, tube connectors 22 can be attached in fluid communication between the interior of sleeve member 12 and the substance so that the substance may be inserted and removed. The threads of sleeve 12 must also have a sealant applied to them if the water jacket is used.

Column 24 can be made to essentially any length and can be as short as 5 mm in length in this embodiment. Because of this feature, invention 10 is ideal for low volume, low back pressure precolumns and guard columns. For example, a packed column 24 of 4.1 mm inside diameter and 5 mm length contributes a volume of less than 60 microliters (ML) to the HPLC system. Band broadening is negligible relative to a typical 15 cm analytical column. The amount of support material used in packing column 24 is so small (for example, less than 0.05 grams of silica) that the packing material can be discarded if column 24 shows signs of becoming plugged or forming a void.

To facilitate a column of any length, sleeve member 12 can be made for different lengths depending upon the length of column 24. If several lengths of brass connectors are available, the same end fittings 14 and 16 can be used to prepare columns 24 of lengths ranging from 5 mm to 30 cm or larger. Also, with conventional fittings, two ferrules and female fittings are required for each unique inside diameter column blank. In another conventional design, a special threaded column blank must be made for each unique inside diameter column. Contrastingly, with the invention 10 disclosed here, the same set of end fittings 14 and 16 can be used for column blanks 24 of different inside diameters. This versatility makes the invention 10 especially attractive for laboratories which pack their own columns. The absence of ferrules also eliminates the possibility of deforming the inside walls of the column blank 24.

The interior design of the column is similar to the design used in most commercial low dead volume columns. Thus, similar column efficiencies can be expected. Efficiency may be slightly improved since mobile phase cannot leak around the frit as it often does when a ferrule forms the seal.

The seal in this invention 10 is formed by compression of ring means 40 between column 24 and end fittings 16 and 18. Thus, the parts that are most likely to be damaged by extensive use or overtightening are the ring means or frits 40 and sleeve members 12. Both of these parts can be replaced easily and cheaply. The columns are easy to assemble and use. Very little torque is necessary to obtain a good seal. In using the preferred embodiment of the invention 10, column 24 was tested and did not leak at pressures below 5000 psi.

It is understood that modifications and alterations can be made in the above described invention while staying within the boundaries of the invention. For example, end fittings 14 and 16 could be secured to sleeve member 12 by means other than threading. Thus it can be seen that the invention achieves at least all of its stated objectives.

What is claimed is:

1. A chromatography column adapted to be used in high performance liquid chromatography comprising:
  (a) an elongated hollow tubular column of rigid material having opposite ends, said column being of generally uniform cylindrical shape free of any permanently affixed threads or fittings;
  (b) a pair of oppositely disposed end fittings each having inner and outer ends and each having elongated longitudinal passageways;
  (c) the longitudinal passageways of said fittings each terminating in an enlarged bore at the respective inner ends thereof;
  (d) a first ring means in said enlarged bores;
  (e) the opposite ends of said column being positioned within said bores in abutting relation to said first ring means;
  (f) an outer tubular sleeve positioned longitudinally around said column; and
  (g) means for securing said end fittings to opposite ends of said sleeve so that said column and first ring means are axially compressed between said pair of secured end fittings with said first ring means being kept in a sealing compressed relationship between said end fittings and said opposite ends of said column.

2. The device of claim 1 wherein said end fittings are cylindrical and have external threads imposed on the outer surface and said tubular sleeve has internal threads imposed on its inner surface so that said end fittings are removably threadable into opposite ends of said sleeve member.

3. The device of claim 2 wherein said outer ends of said end fittings comprise nut elements so that said end fittings can be threaded into said sleeve element by grasping and turning said nut elements with a wrench means.

4. The device of claim 1 wherein said end fittings have internal threads imposed upon the inside of said longitudinal passageways at said outer ends so as to be threadably mateable with threaded male ends of threaded nut fittings which are positioned at the ends of tubes connected said column in fluid communication with a high performance liquid chromatography system.

5. The device of claim 1 wherein said first ring means comprises a fluorocarbon-encased stainless steel frit.

6. The device of claim 1 wherein said outer tubular sleeve is made of brass.

7. The device of claim 1 wherein said tubular column is made of stainless steel.

8. The device of claim 1 wherein a second ring means is retentatively held in a radial slot in said enlarged bore of one of said end fittings, said second ring means being of a resilient material having an inside diameter which resiliently allows said tubular column to pass through and abut said first ring means but retentively holds said tubular column so that upon disengagement of the opposite said end fitting, said tubular column remains in an abutting relationship with said first ring means in said end fitting.

9. The device of claim 1 wherein said longitudinal passageways of said end fittings have various diameter bore sections.

10. The device of claim 1 further comprising tubular members sealingly attached to apertures in the side walls of said tubular sleeve, said tubular members being in fluid communication at one end with the interior space of said sleeve member between said sleeve member and said tubular column and at the other end with a liquid.

11. The device of claim 1 wherein said end fittings further comprise channels on opposite sides of said longitudinal passageways at said outer ends and extend inwardly toward said inner ends along said longitudinal passageways such a distance so as to allow tweezer means to remove said first ring means.

12. The device of claim 8 wherein said end fitting having said radial slot further comprises channels on opposite sides of and extending inwardly along said longitudinal passageways from said outer end of said end fitting such a distance so as to allow tweezer means to be inserted in said channels to remove said first ring means or said second ring means or both.

13. The device of claim 3 wherein the length of said tubular sleeve is such that said fittings can be in tight abutting engagement with said first ring means to seal said first ring means against the ends of said column without said nuts engaging the ends of said tubular sleeve, said end fittings and said tubular sleeve being free from any sealing means therebetween except for said threads.

* * * * *